United States Patent [19]

Esko et al.

[11] Patent Number: 5,639,734
[45] Date of Patent: Jun. 17, 1997

[54] DISACCHARIDE INFLAMMATION INHIBITORS AND USES THEREOF

[76] Inventors: Jeffrey D. Esko, 1220 30th St. South, Birmingham, Ala. 35205; Arun K. Sarkar, 4114 Elder Oaks Ways, Apt. D, Birmingham, Ala. 35209

[21] Appl. No.: 359,582

[22] Filed: Dec. 20, 1994

[51] Int. Cl.$^6$ .......................... A61K 31/70; C07H 15/00; C07H 17/00
[52] U.S. Cl. .................. 514/25; 514/24; 514/53; 514/54; 514/61; 514/62; 536/4.1; 536/17.2; 536/17.9; 536/18.7; 536/53; 536/54; 536/55; 536/55.1; 536/55.2; 536/123.1; 536/123.13
[58] Field of Search ......................... 536/4.1, 17.2, 536/17.9, 123.1, 123.13, 18.7, 53, 54, 55, 55.1, 55.2; 514/24, 25, 53, 54, 61, 62

[56] References Cited

U.S. PATENT DOCUMENTS 5,426,178  6/1995  Laine et al. ........................ 536/1.11

OTHER PUBLICATIONS

Lasky *Science*, 1992, 258, 964–969.

*Primary Examiner*—John Kight
*Assistant Examiner*—Kathleen Kahler Fonda
*Attorney, Agent, or Firm*—Benjamin Aaron Adler

[57] ABSTRACT

The present invention provides a composition of matter comprising a biosynthetic anti-inflammatory oligosaccharide, comprising the structure of: sugar - sugar - X - R; wherein said sugar is selected from the group consisting of N-acetylneuraminic acid, galactose, N-acetylglucosamine, N-acetylgalactosamine, fucose and mannose; wherein X is a bridging atom selected from the group consisting of oxygen, sulfur, nitrogen and carbon; and wherein R is an aglycone selected from the group consisting of naphthol, naphthalenemethane, indenol, a heterocyclic derivative of indenol, a heterocyclic derivative of naphthol and a heterocyclic derivative of naphthalenemethanol. Also provided is a method of treating an inflammatory disease in an individual comprising the step of administering to said individual a therapeutically effective dose of the novel composition of the present invention.

18 Claims, 6 Drawing Sheets

DISACCHARIDE INFLAMMATION INHIBITORS AND USES THEREOF

BACKGROUND OF THE INVENTION

1. Field of the Invention

The present invention relates generally to the fields of inflammation and carbohydrate and glycoprotein chemistry. More specifically, the present invention relates to novel disaccharide inhibitors of inflammation.

2. Description of the Related Art

During an inflammatory response, leukocytes move from the circulation into tissues to destroy foreign organisms and to clear damaged tissue. The first step in this process involves binding of leukocytes to cytokine activated endothelial cells lining the post-capillary venules. Activation of the endothelium causes the expression of cell surface proteins belonging to the selectin family of adhesion molecules. Vascular endothelial cells express E-selectin when induced by cytokines such as TNF-$\alpha$, IL-1 or LPS and P-selectin when stimulated by thrombin or histamine. Monocytes, neutrophils and lymphocytes express L-selectin. Each selectin contains a short C-terminal cytoplasmic tail, a single transmembrane domain, an EGF-like domain, and a variable number of short consensus repeats like those found in complement regulatory proteins. The amino terminal end contains a C-type lectin domain that binds carbohydrate ligands in a $Ca^{2+}$-dependent manner. The lectin binding domain recognizes specific carbohydrate structures, such as sialyl Lewis$^x$ (sLe$^x$) present on leukocytes or sulfated ligands on the endothelium. The affinity of the interaction varies considerably and may depend on the conformation and valency of the ligand as well as differences in the carbohydrate recognition domains of the different selectins. Glycoprotein ligands identified by affinity purification contain clustered oligosaccharide chains, although monovalent carbohydrate ligands can bind as well.

Leukocytes expressing sLe$^x$ bind to activated endothelium expressing E- or P-selectins. L-selectins on the leukocytes bind to carbohydrate ligands on the endothelium such as sulfo- Lewis antigens and possibly glycosaminoglycans. The interaction results in leukocyte rolling along the endothelium. Stronger adhesion develops sequentially through chemo-attractant signaling and integrins on the leukocytes binding to intercellular adhesion molecules (ICAMS) on endothelial cells. The leukocytes subsequently extravasate across the endothelium and into the tissue.

The evidence for selectins mediating leukocyte extravasation and inflammation in vivo is compelling. Studies of selectin knock-out mice showed the absence of leukocyte rolling and a delay in neutrophil extravasation into the peritoneum. Human patients with leukocyte adhesion deficiency syndrome fail to produce sLe$^x$ and related structures and their leukocytes do not roll properly on activated endothelium. The latter study points to the importance of fucosylated ligands in selectin binding.

Sometimes the inflammatory response goes awry and destroys normal tissue. Enhanced expression of E-selectin and P-selectin occurs in the vascular endothelium of synovial tissue from rheumatoid arthritis patients. As a consequence, endothelial cells become adhesive towards monocytes, neutrophils and lymphocytes. These cells extravasate from the vessel lumen into the synovial tissue and joint fluids. The subsequent release of proteases and reactive oxygen species results in degradation of cartilage, which further exacerbates the inflammatory process and the cycle continues. Blocking the transendothelial migration of leukocytes provides a way to treat chronic inflammatory arthritis.

Selectins also play a role in the acute inflammatory response to reperfusion injury, cutaneous wounding, infection, and various models of induced lung damage. Thus, intense interest exists in developing inhibitors of selectin-carbohydrate interactions. One strategy consists of using soluble forms of selectins as competitive receptors or monoclonal antibodies directed against selectins or sLe$^x$. These agents block neutrophil adhesion to endothelial cells in vitro and inhibit inflammation in vivo. Oligosaccharides related to Lewis X and Lewis A and inositol polyanions also inhibit leukocyte rolling on vessel endothelia and decrease inflammation.

Glycosylation inhibitors are used to study the biological function of glycoconjugates in animal cells. Plant alkaloids such a swainsonine and deoxynojiromycin derivatives block glycoprotein biosynthesis in vivo by inhibiting glycosidases involved in the maturation of Asn-linked oligosaccharides. Recently, an exocyclic epoxide derivative of glycosylceramide was shown to inhibit glycosphingolipid biosynthesis in cells, presumably by making a covalent adduct to a galactosyltransferase that acts on the ceramide intermediate. A number of other substrate-based inhibitors have been described that block glycosyltransfersases in vitro, but poor uptake has prevented them from inhibiting glycosylation in vivo.

Another class of inhibitors consist of glycosides that resemble biosynthetic intermediates involved in glycoconjugate assembly. These compounds act as substrates, produce free oligosaccharides, and divert the assembly of chains from glycoconjugates to the added acceptors. The first type of inhibitors in this class was described over twenty years ago by Okayama et al. *Biochem. J.* (Tokyo) 74:1069–1073 (1973). They showed that $\beta$-D-xylosides stimulate the synthesis of free glycosaminoglycan (GAG) chains and competitively inhibit glycosaminoglycan formation on proteoglycan core proteins. The free glycosaminoglycan chains can have desirable biological properties as well. For example, heparan sulfate chains produced on Xyl$\beta$-0-2-naphthol (naphthol-$\beta$-D-xyloside) will bind to basic fibroblast growth factor, facilitating its interaction with high affinity receptors. In a similar way, GalNAc-O-benzyl stimulates mucin oligosaccharide synthesis and inhibits O-linked glycoprotein synthesis. Altering glycoprotein synthesis in HL-60 cells in this way inhibits the expression of sialyl Lewis X (sLe$^x$) ligands and adhesion to activated endothelial cells. Acceptors consisting of two or more sugars would be desirable and more selective since many glycosyltransferases use disaccharides or larger oligosaccharides as substrates. However, poor transfer of disaccharides across cell membranes severely limits this approach.

The prior art is deficient in the lack of effective means of inhibiting the inflammatory response. The present invention fulfills this longstanding need and desire in the art.

SUMMARY OF THE INVENTION

In one embodiment of the present invention, there is provided a composition of matter comprising a biosynthetic anti-inflammatory oligosaccharide, comprising the structure of: sugar - sugar - X - R; wherein said sugar is selected from the group consisting of N-acetylneuraminic acid, galactose, N-acetylglucosamine, N-acetylgalactosamine, fucose and mannose; wherein X is a bridging atom selected from the group consisting of oxygen, sulfur, nitrogen and carbon; and wherein R is an aglycone selected from the group consisting of naphthol, naphthalenemethane, indenol, a heterocyclic derivative of indenol, a heterocyclic derivative of naphthol and a heterocyclic derivative of naphthalenemethanol.

In another embodiment of the present invention, there is provided a pharmaceutical composition, comprising the novel biosynthetic anti-inflammatory composition of the present invention and a pharmaceutically acceptable carrier.

In yet another embodiment of the present invention, there is provided a method of treating an inflammatory disease in an individual comprising the step of administering to said individual a therapeutically effective dose of the composition of the present invention.

In still yet another embodiment of the present invention, there is provided a method of regulating the synthesis of a naturally occurring saccharide in a cell, comprising the step of contacting said cell with a pharmacologically effective amount of the composition of claim 1.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 4A shows cells that were treated with a non-specific mouse IgM. FIG. 4B shows cells that were treated with CSLEX-1. FIG. 4C shows cells that were treated with NDV sialidase before reacting them with CSLEX-1. FIG. 4D shows cells that were grown in medium containing 200 μM acetylated Galβ1→4GlcNAcβ-O-naphthalenemethanol before reacting them with CSLEX-1.

DETAILED DESCRIPTION OF THE INVENTION

Figure 1:
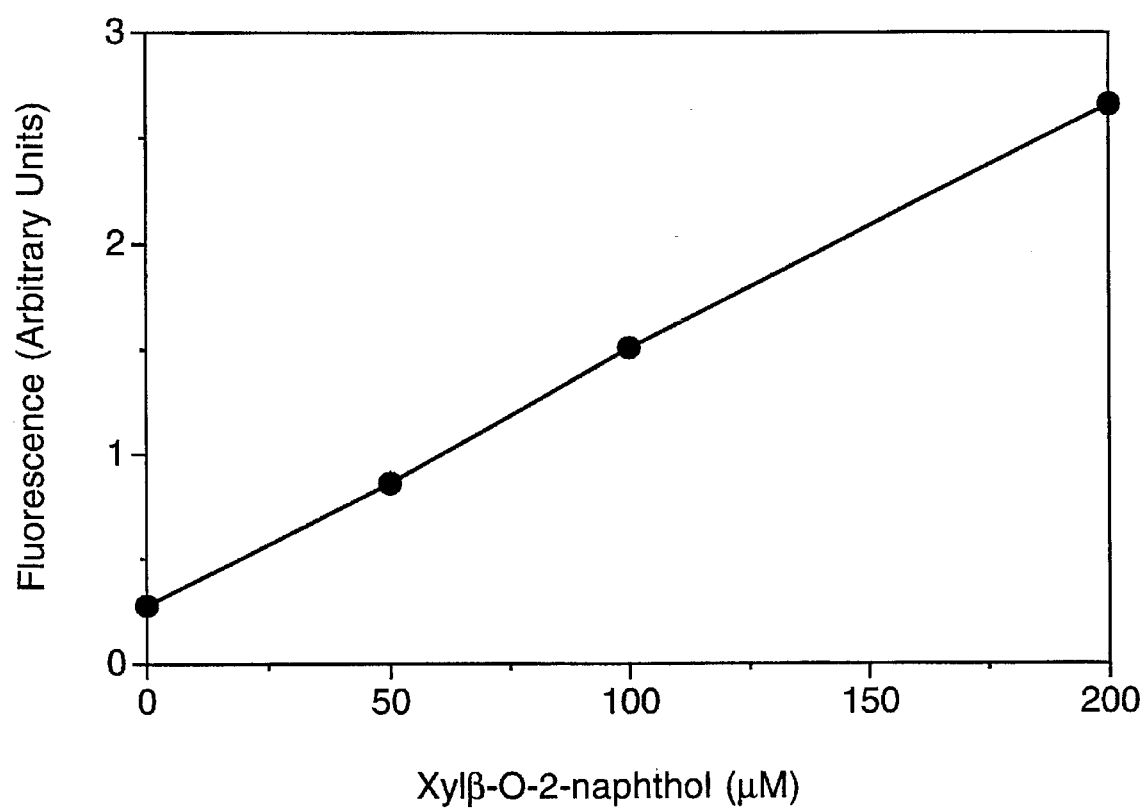
FIG. 1 shows the uptake of Xylβ-0-2-naphthol by Chinese hamster ovary cells occurs by diffusion. Confluent monolayers of Chinese hamster ovary cells were incubated with the indicated concentrations of Xylβ-0-2-naphthol at 37° C. for 30 minutes. The amount of glycoside taken up was determined by fluorescence assay.

The present invention provides novel disaccharide antagonists of inflammation, i.e., these modified disaccharides may be used as anti-inflammatory agents. The present invention comprises new disaccharides that prime oligosaccharides in cells. The disaccharides are modified so that they diffuse across cell membranes and enter the subcellular compartments where glycosylation takes place. They act as substrates for various glycosyltransferases depending on the types of sugars present. The priming of oligosaccharides on the disaccharides diverts the assembly of chains from glycoproteins and glycolipids to the primers and thus inhibits the formation of glycoconjugates in cells. In the present invention, it was shown that decreasing the number of free hydroxyl groups to less than 5 solves the problem of poor uptake for dissacharides linked to 2-naphthol. Acetylation of the sugars also allows disaccharides to enter the Golgi and prime oligosaccharide chains. Unless otherwise noted, the sugars were in the D-configuration and were in the pyranose form.

Some of the carbohydrate chains found on glycoproteins and glycolipids participate in cell adhesion reactions that cause inflammation. Leukocytes express sialylated and sulfated Lewis X carbohydates on glycoproteins and glycolipids (TABLE I). These ligands bind to plasma membrane receptors (selectins) expressed by endothelial cells. The interaction between the selectin and the carbohydrate ligand causes leukocytes in the circulation to roll along the endothelium and eventually extravasate into the tissue. Available antagonists of this interaction include monovalent and multivalent forms of the Lewis carbohydrates, mimetics of sialylated Lewis X, antibodies prepared against the selectins and soluble recombinant forms of selectins. These agents block leukocyte adhesion in cell culture and leukocyte extravasation and inflammation in vivo.

The present invention provides disaccharides that resemble biosynthetic intermediates involved in the formation of Lewis carbohydrates. The disaccharides inhibit the formation of the glycoprotein ligands for selectins by diverting the synthesis of the carbohydrate chains from the proteins or lipids to the disaccharide primers. Thus, the mode of action of the novel compounds of the present invention is entirely different than any available method for treating selectin-mediated cell adhesion and inflammation.

The novel compounds of the present invention may be used to treat both acute and chronic inflammatory diseases. Representative examples of acute inflammatory diseases include appendicitis, tonsilitis, delayed hypersensitivity reactions, inflammation due to sepsis, cutaneous inflammation and ischemic reperfusion injury. Representative examples of chronic inflammatory diseases include rheumatoid arthritis. Certain tumor cells produce sialylated Lewis carbohydrates that play a role in tumor cell invasion and metastasis. Thus, the invention would be useful as an adjunct to conventional chemotherapy.

The present invention encompasses a number of compounds since the structures of the oligosaccharides found on glycoproteins and glycolipids are complex. In general, Lewis X and Lewis A carbohydrates recognized by selectins assemble on the ends of polylactosaminoglycan chains. Thus, the disaccharides that are specifically contemplated by the present invention include elements of polylactosaminoglycans and Lewis X and Lewis A carbohydrates.

The present invention is directed to a composition of matter comprising a biosynthetic anti-inflammatory oligosaccharide, comprising the structure of: sugar - sugar - X - R; wherein said sugar is selected from the group consisting of N-acetylneuraminic acid, galactose, N-acetylglucosamine, N-acetylgalactosamine, fucose and mannose; wherein X is a bridging atom selected from the group consisting of oxygen, sulfur, nitrogen and carbon; and wherein R is an aglycone selected from the group consisting of naphthol, naphthalenemethane, indenol, a heterocyclic derivative of indenol, a heterocyclic derivative of naphthol and a heterocyclic derivative of naphthalenemethanol.

The disaccharides may be acylated with, e.g., acetyl, butyryl or benzoyl groups to reduce their hydrophilicity and make them permeable to cell membranes. Two of the disaccharides (acetylated Galβ1→4GlcNAcβ-O-naphthalenemethanol and acetylated GlcNAcβ1→3Galβ-O-naphthalenemethanol) have been shown to prime oligosaccharides in cultured cells and to inhibit the formation of sialyl Lewis X in HL-60 human promyelocytic leukemia cells (TABLE I). The various disaccharides described above and their acylated or aryl derivatives are logical extensions of the present invention. In addition, analogs of the above compounds in which critical hydroxyl groups are missing or alkylated would bind to glycosyltransfersase and inhibit their activity.

The novel biosynthetic anti-inflammatory polysaccharide composition of the present invention may also contain a methyl group attached to a hydroxy group. For example, a methyl group may be attached to any of the hydroxyl groups of the sugars. In addition, in the novel biosynthetic anti-inflammatory polysaccharide composition of the present invention, the sugar may have a sulfur substituted for an oxygen. For example, it may be preferably to substitute the 5-OH group of the sugar with a sulfur atom.

Representative examples of the novel biosynthetic anti-inflammatory polysaccharide composition of the present invention include (1)N-acetylglucosamineβ1→6N-acetylgalactosamine α-X-R; (2) N-acetylglucosamineβ1→6 galactoseβ-X-R; (3) N-acetylglucosamineβ1 →6mannoseα-X-R; (4) N-acetylglucosamineβ1→2mannoseα-X-R; (5) galactoseβ1→3N-acetylgalactosamineα-X-R; (6) galactoseβ1→4N-acetylglucosamineβ-X-R; (7) fucoseα1→4N-acetylglucosamineβ-X-R; (8) fucoseα1→3N-acetylglucosamineβ-X-R, wherein for all of the above-mentioned compositions O is a bridging atom selected from the group consisting of oxygen, sulfur, nitrogen and carbon; and wherein R is an aglycone selected from the group consisting of naphthol, naphthalenemethane, indenol, a heterocyclic derivative of indenol, a heterocyclic derivative of naphthol and a heterocyclic derivative of naphthalenemethanol.

The present invention is also directed to a method of treating an inflammatory disease in an individual comprising the step of administering to said individual a therapeutically effective dose of the novel biosynthetic anti-inflammatory polysaccharide pharmaceutical composition of the present invention. Generally, the compositions of the present invention may be used to treat a wide variety of inflammatory disease. Representative examples of inflammatory diseases include acute inflammatory diseases and chronic inflammatory diseases. Representative examples of acute inflammatory disease include appendicitis, tonsilitis, delayed hypersensitivity reactions, inflammation due to sepsis, cutaneous inflammation and ischemic reperfusion injury. Representative examples of a chronic inflammatory disease includes rheumatoid arthritis. Generally, the composition of the present invention may be administered at any concentration which reduced inflammation in the target individual. Preferably, said composition is administered in a dose of from about 0.1 mg/kg to about 20 mg/kg.

The present invention is also directed to a method of regulating the synthesis of a naturally occurring saccharide in a cell, comprising the step of contacting said cell with a pharmacologically effective amount of the the novel biosynthetic anti-inflammatory polysaccharide pharmaceutical composition of the present invention. Novel biosynthetic polysaccharides may be designed, using the teachings of the present invention, to disrupt the synthesis of a wide variety of naturally occuring substances, particularly saccharides. For example, the present invention provides a composition which disrupts the synthesis of a saccharide which binds to a selectin. Representative examples of such saccharides include N-acetylneuraminic acidα2→3 galactoseβ1→4 (fucoseα1→3) N-acetylglucosamineβ-X-R, N-acetylneuraminic acidα2→3galactoseβ1→4 N-acetylglucosamineβ1-3galactoseβ1→4 (fucoseα1→3) N-acetylglucosamineβ-X-R, N-acetylneuraminic acidα2→3 galactose β1→4 (fucoseα1-3) N-acetylglucosamine β1-galactoseβ1→4 (fucoseα1→3) N-acetylglucosamineβ-X-R, N-acetylneuraminic acidα2→3 galactoseβ1→3 (fucoseα1→4) N-acetylglucosamineβ-X-R, SO$_4$-3 galactoseβ1→4(fucoseα1→3) N-acetylglucosamineβ-X-R, SO$_4$- 3 galactoseβ1→3(fucoseα1→4) N-acetylglucosamineβ-X-R, N-acetylneuraminic acidα2→3 (SO$_4$-6) galactoseβ1→4 (fucoseα1→3)N-acetylglucosamineβ-X-R; wherein X is a bridging atom selected from the group consisting of oxygen, sulfur, nitrogen and carbon; and wherein R is an aglycone selected from the group consisting of naphthol, naphthalenemethane, indenol, a heterocyclic derivative of indenol, a heterocyclic derivative of naphthol and a heterocyclic derivative of naphthalenemethanol. Generally, the composition of the present invention may be administered at any concentration which regulates the synthesis of a naturally occurring saccharide in a cell in the target individual. Preferably, said composition is administered in a dose of from about 0.1 mg/kg to about 20 mg/kg.

It is specifically contemplated that pharmaceutical compositions may be prepared using the novel biosynthetic anti-inflammatory composition of the present invention. In such a case, the pharmaceutical composition comprises the novel biosynthetic anti-inflammatory composition and a pharmaceutically acceptable carrier. A person having ordinary skill in this art would readily be able to determine, without undue experimentation, the appropriate dosages and routes of administration of the novel biosynthetic anti-inflammatory composition of the present invention.

The following examples are given for the purpose of illustrating various embodiments of the invention and are not meant to limit the present invention in any fashion.

EXAMPLE 1

Synthesis of glycosides

The synthesis of Xylβ-0-2-naphthol and L-Araα-0-2-naphthol has been described. Galβ-0-9-phenanthrol, Galβ1→3Galβ-0-9-phenanthrol, Galβ1→3Galβ-0-2-naphthol, and Galβ1→3 Galβ-0-9-naphthol were prepared by reacting the bromo sugar with the sodium salt of the alcohol. Xylβ1→6Galβ-0-2-naphthol was obtained by reacting acetobromoxylose with Galβ-0-2-naphthol (Sigma) in presence of silver carbonate. The dissacharide intermediate Xyl(Ac)$_3$β1→6Galβ-0-2-naphthol was partially methylated by reaction with trimethyloxonium tetrafluoroborate in the presence of 2, 6-di(tertiarybutyl)trimethyl pyridine and the acetyl groups were subsequently removed with sodium methoxide. Galβ1→3GlcNAcβ-0-napthalenemethanol was made by coupling acetylated Galβ-S-C$_2$H$_5$ and 2,3 -di-0-benzoylGlcNAclβ-0-naphthalenemethanol followed by deacetylation with sodium methoxide. Acetylation of sugars was performed with acetic anhydride in pyridine. All compounds were purified by silicic acid chromatography and their structures were confirmed by both $^1$H-NMR and $^{13}$C-NMR. They were more than 95% pure by NMR and by sulfuric acid charring on thin-layer plates.

EXAMPLE 2

Cell Culture

Chinese hamster ovary cells (Chinese hamster ovary-K1, CCL 61), mouse embryonal carcinoma cells (F9, CRL 1720), and human promyelocytic leukemia cell (HL-60, CC1240) were obtained from the American Type Culture Collection in Rockville Md. Wild type Chinese hamster ovary cells and the xylosyltransferase deficient mutant pgsA-745 were maintained in Ham's F-12 medium containing 7.5% (v/v) fetal bovine serum (Hyclone Laboratories, Salt Lake City, Utah), 100 U/ml penicillin, and 100 µg/ml of streptomicin sulfate as described previously. F9 cells were grown in DMEM containing 12.5% (v/v) fetal bovine serum and antibiotics on plates were coated with a solution of 0.1% (w/v) gelatin as described previously. HL-60 cells were maintained in suspension in RPMI-1640 medium.

EXAMPLE 3

Uptake Studies

Compounds were dissolved in DMSO and added to growth medium such that the final concentration of vehicle was 0.5% (v/v). Confluent cells were incubated with supplemented growth medium at 37° C. for various times. The cultures were placed on ice, the medium was aspirated and the cells were washed three times with cold PBS containing 1 mg/ml of bovine serum albumin. Cells were solubilized in a small volume of 0.1M NaOH and the extracts were neutralized with one mole equivalent of acetic acid. After centrifuging the samples, the supernatants were applied to Sep-Pak Plus C18 cartridges (Waters Associates) and washed with water (10 ml) and 20% (v/v) methanol in water (5 ml). Bound material was eluted with 5 ml of 40% (v/v) methanol in water and concentrated to dryness. The residue was dissolved in methanol and its fluoresence was measured (SLM-Aminco Instruments). The excitation and emission wavelengths for 2-naphthol derivatives were 293 nm and 395 nm, respectively. Phenanthrol derivatives were excited at 310 nm and the emission was measured at 365 nm. The fluorescence for 9-phenanthrol derivatives was corrected for a 2.6 fold greater intensity compared to comparable naphthol derivatives.

Uptake of Galβ1→4GlcNAcβ-0-2-naphthalenemethanol was measured in the same way except that the cells were scraped from the plate and protein and nucleic acid were precipitated with 10% (w/v) trichloroacetic acid in the cold. The sample was centrifuged and the supernatant was applied to a Sep-pak C18 cartridge. The cartridge was first washed with water (10 ml), 5% (v/v) methanol in water (5 ml) and finally with 60% (v/v) methanol in water (5 ml). The latter was concentrated to dryness and the residue was dissolved in methanol to measure its fluorescence.

EXAMPLE 4

Priming of oligosaccharides

Priming of glycosaminoglycan chains was measured in pgsA-745 cells deficient in xylosyltransfersase. The cells were grown to confluence in 96-well microtiter plates (Falcon). Fresh medium (0.2 ml) containing 50 µCi/ml of H$_2$$^{35}$SO$_4$ (25–40 Ci/mg) and the test compounds were added to the wells. The top row of wells contained 500 µl of glycoside and each subsequent row contained a serial dilution (1:3$^n$, v/v). Cells were incubated for 5 hours at 37° C. and solubilized by adding 20 µl of 0.5M NaOH. The individual wells were adjusted to 0.2% (w/v) Zwittergent 3–12, 25 µg/ml chondroitin sulfate, 0.2M acetic acid and 10 mM Na$_2$SO$_4$. The samples were transferred to a GeneScreen Plus membrane (Dupont-NEN) placed on top of a piece of 1Chr paper on a vacuum Minifold (Schleicher & Schuell). A wash solution of 0.2% (w/v) Zwittergent 3–12, 0.2M acetic acid and 10 mM Na$_2$SO$_4$ (0.5 ml) was passed through each well. The membranes were removed from the Minifold, soaked for 5 minutes in 20 ml of wash solution, air-dried and exposed to RX X-ray film for 10–18 hours.

Priming of oligosaccharides on Galβ1→4GlcNAcβ-0-2-naphthalenemethanol was measured in F9 cells grown on gelatin-coated 6-well plates. The medium was replaced with low-glucose (4.5 g/L) DMEM containing 15% (v/v) fetal bovine serum, antibiotics, test compounds, and 10 µCi/ml of (6-$^3$H-glucosamine HCl (33.3 Ci/mmol, Dupont-NEN). After 24 hours at 37° C., the plate was chilled on ice, the medium was separated from the cells and the monolayer was washed with 3 ml of buffer containing 140 mM NaCl, 4 mM KCl and 20 mM hepes (pH 7.2). The media and wash solution were centrifuged to remove cell debris and the supernatant was applied to a Sep-Pak C18 cartridge. The cartridge was washed with 0.5M NaCl (10 ml, water (50 ml) and then with 40% (v/v) methanol in water (5 ml). The latter fraction was dried, dissolved in water and counted by liquid scintillation spectrometry. A portion of the material was analyzed by anion-exchange chromatography using QAE-Sephadex before and after treating with NDV sialidase.

EXAMPLE 5

Fluorescence activated cell sorting analyses

HL-60 cells were incubated with or without 200 μM peracetylated Galβ1→4GlcNAcβ-0-2-naphthalenemethanol for 40 hours in RPMI-1640 medium supplemented with 10% fetal bovine serum. Cells were centrifuged, washed with PBS containing 2% serum and 0.5% sodium azide, and then incubated for 30 minutes at 4° C. with the anti-sLe$^x$ mAb CSLEX-1. The cells were washed twice and then incubated for 30 minutes at 4° C. with an FITC-conjugated goat anti-mouse IgM for 30 minutes at 4° C. Cells were washed again, resuspended in PBS containing 1% (v/v) paraformaldehyde and analyzed by fluorecence activated cell sorting. Human IgG was present in all incubations (2 mg/ml). A mouse non-specific IgM was used as a control antibody. In one experiment, the cells were treated with Oxford Glycosystems NDV sialidase (10 mU, 1 hour, 37° C.) in 50 mM medium acetate buffer (pH 5.5) before reacting the cells with CSLEX-1.

EXAMPLE 6

Uptake of Xylβ-0-2-naphthol in Chinese hamster ovary cells

Figure 2:
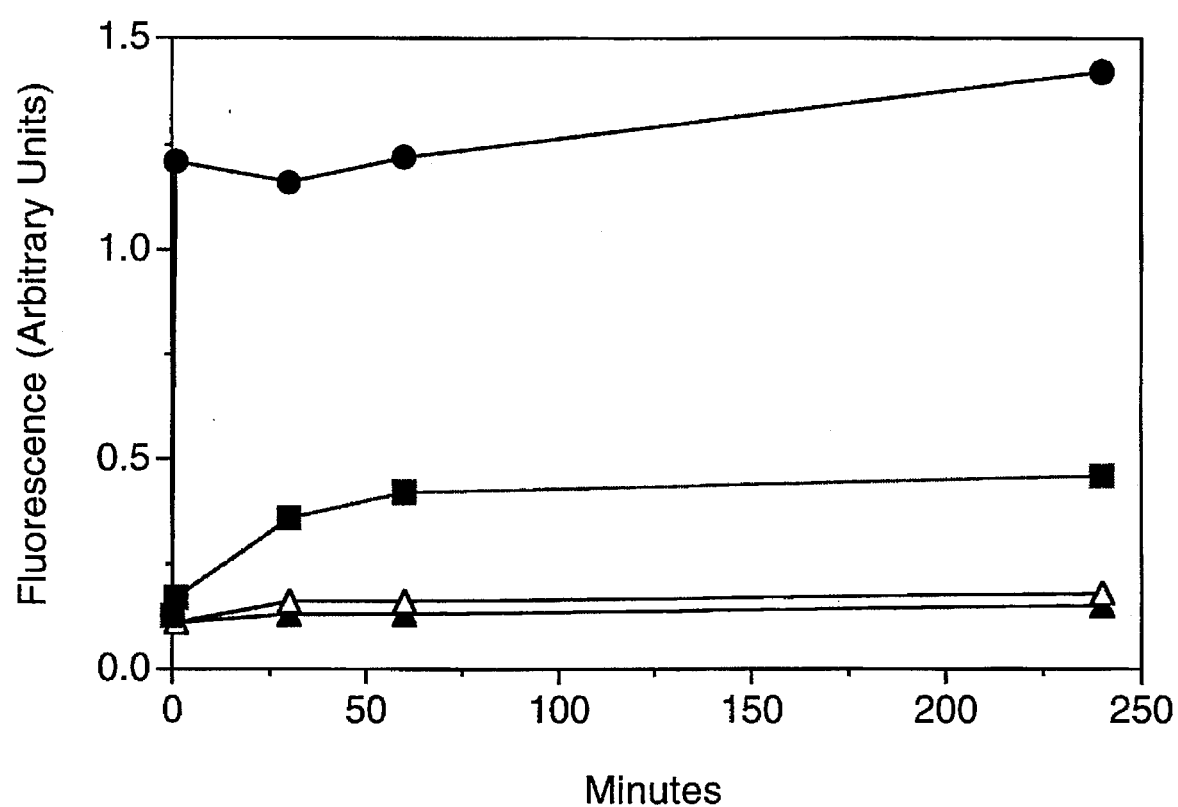
FIG. 2 shows the uptake of glycosides by Chinese hamster ovary cells varies with the size of the glycan. The various glycosides were added (100 μM) to confluent Chinese hamster ovary cell monolayers and at the times indicated, the amount of glycoside taken up was quantitated by fluorescence assay. Filled circles: Xylβ-0-2-naphthol; filled square: Galβ-0-2-naphthol; unfilled triangle: Galβ1→4Xylβ-0-2-naphthol; filled triangle: Galβ1→3Galβ0-2-naphthol.

Animal cells take up β-D-xylosides and prime glycosaminoglycan chains with great efficiency. For priming to occur, the glycoside must pass though the plasma membrane and enter the Golgi where the glycosyltransferases reside. To demonstrate the uptake of Xylβ-0-2-naphthol in Chinese hamster ovary cells, a fluorescence assay was used. Uptake depended on concentration and did not saturate, suggesting that it was diffusion limited (FIG. 1). Uptake also was rapid and the amount associated with cells reached a plateau in less than one minute (FIG. 2). In contrast, Xylβ-0-2-naphthol, the uptake of Galβ-0-2-naphthol was slow and reached a lower steady-state level. Xylβ-0-2-naphthol has three hydroxyl groups, whereas Gal-0-2-naphthol has four. Therefore, the presence of one additional hydroxyl group reduced both the rate and the extent of uptake. Dissaccharides such as Galβ1→4Xylβ-0-2-naphthol (six hydroxyls) and Galβ1→3Galβ-0-2-naphthol (seven hydroxyls) were not taken up al all (FIG. 2).

Other glycosides showed that L-Araβ-0-2-naphthol was taken up nearly as well as Xylβ-0-2-naphthol (0.8 vs. 1.0 unit of fluorescence). Changing the aglycone from 2-naphthol to 9-phenanthrol stimulated the uptake of galactoside (0.3 vs 4.2 units) to a level greater than observed for Xylβ-0-2-naphthol (1.0 unit). However, Galβ1→3Galβ-0-2-phenanthrol was not taken up (less than 0.1 unit). Thus, the added aromatic ring in phenanthrol was sufficient to overcome the extra hydroxyl group in a hexoside (4 versus 3 hydroxyls) but not the multiple hydroxyl groups in a disaccharide (7 hydroxyls).

EXAMPLE 7

Criticality of hydroxyl group number

To demonstrate the maximum number of hydroxyl groups that a naphthol glycoside can have, a disaccharide consisting of Xylβ1→6Galβ-0-2-naphthol (six hydroxyls) was synthesized. Since Xylβ-0-2-naphthol efficiently primes glycosaminoglycan chains, the disaccharide would behave similarly if it diffused across cell membranes into the ER/Golgi network. Therefore, uptake of the disaccharide was measured indirectly by the determining the incorporation of $^{35}SO_4$ into glycosaminoglycan chains. To distinguish glycosaminoglycans produced on the glycoside from those made on endogenous proteoglycans, a Chinese hamster ovary cell mutant deficient in xylosyltransferase was made. The enzymatic deficiency blocks glycosaminoglycan synthesis on endogenous core proteins, but does not prevent chain synthesis on synthetic β-D-xylosides. [$^{35}S$] glycosaminoglycan synthesis was measured by incubating mutant cells in a 96 well plate with glycoside derivatives at different doses. The cells and spent media were then transferred to a positively charged nylon membrane to detect newly made chains by autoradiography.

Figure 3:
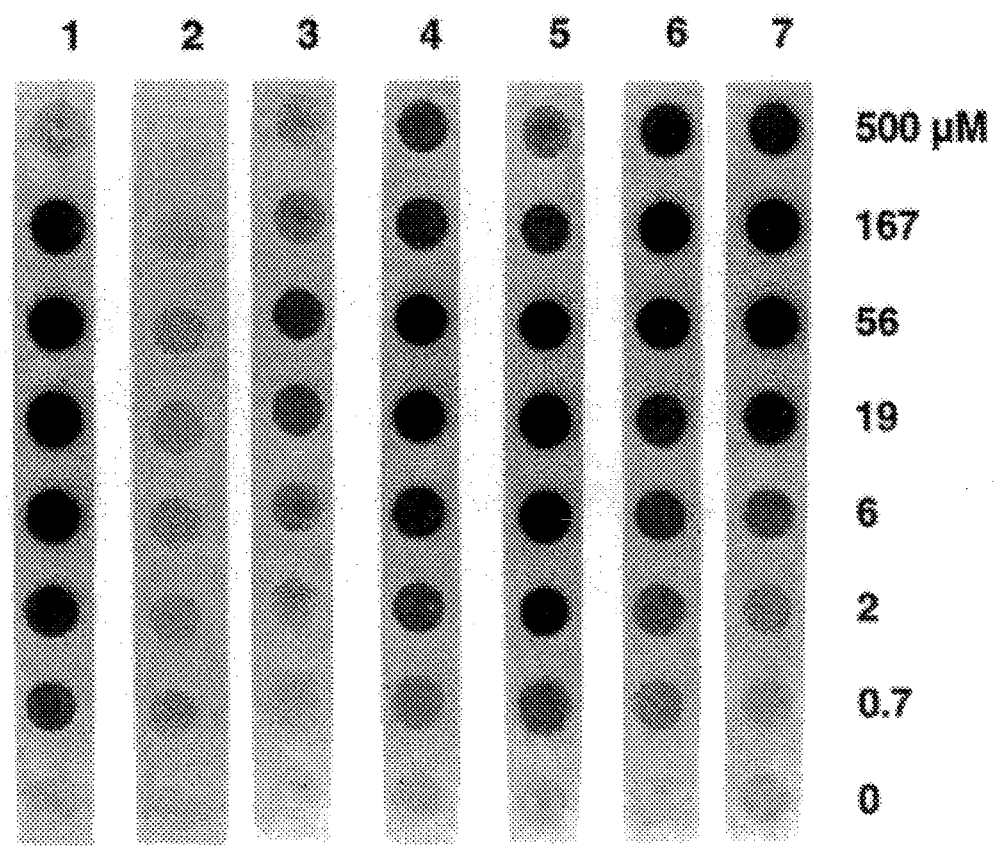
FIG. 3 shows the priming of glycosaminoglycans by acetylated glycosides. Various compounds at the indicated concentrations were provided to confluent Chinese hamster ovary cells in a 96 well plate. Glycosaminoglycan synthesis was measured by autoradiography of [$^{35}$S]-glycosaminoglycan collected on a postively charged nylon membrane. 1: Xylβ-0-2-naphthol; 2: Xylβ1→6Gal-0-2-naphthol; 3: Xylβ1→6Gal(Me)-0-2-naphthol; 4: Xylβ1→6Gal(Me)$_2$-0-2-naphthol; 5: Xylβ1→6Gal(Me)$_3$-0-2-naphthol; 6: Xyl(Ac)$_3$β-0-2-naphthol; 7:Xyl(Ac)$_3$β1→6Gal(Ac)$_3$-0-2-naphthol.

The disaccharide (Xylβ1→6Galβ-0-2-naphthol, 6 hydroxyls) did not prime [$^{35}S$]-glycosaminoglycans even at 500 μM, the highest concentration tested (FIG. 3, lane 2). In contrast, Xylβ-0-2-naphthol primed chains efficiently (lane 1). A series of methylated derivatives of the disaccharide was then synthesized in which the internal Gal residue contained one, two, or three methyl groups attached randomly to the 2-OH, 3-OH or 4-OH positions. Blocking one of the hydroxyls with a methyl group (Xylβ1→6Gal (Me) β-0-2-naphthol, 5 hydroxyls) stimulated $^{35}S$glycosaminoglycan synthesis with a maximum effect at approximately 60 μM (lane 3). Higher concentrations were less effective possibly due to the detergent proeprties of the glycoside. The dimethylated derivative (Xylβ1→6Gal (Me)β-0-2-naphthol, 4 hydroxyls) primed a much lower concentrations (2–6 μM, lane 4). The trimethylated derivative (Xylβ1→6Gal (Me)β-0-2-naphthol, 3 hydroxyls) primed at less than 1 μM (lane 5), nearly as well as Xylβ-0-2-napthol (3 hydroxyls, lane 1). Thus, five or more free hydroxyl groups limits uptake and utilization of naphthol disaccharides under these conditions.

Acetylation provides another way to block hydroxyl groups and to render sugars more hydrophobic. As shown in FIG. 3, Xyl(Ac)$_3$β-0-2-naphthol primed glycosaminoglycans in Chinese hamster ovary cells, although somewhat less effectively than the non-acetylated compound (compare lanes 1 and 6). Similarly, peracetylated Xylβ1→6Galβ-0-2-naphthol primed glycosaminoglycan chains, even at concentrations as low as ~6 μM (lane 7).

The present invention also demonstrates that acetylation of Galβ1→4GlcNAcβ-0-2-naphthalenemethanol and GlcNAcβ1-3Galβ-0-2-naphthalenemethanol would result in priming of oligosaccharides in F9 embryonal carcinoma cells. These cells make polylactosaminoglycan chains and sialyl Lewis X (sLe$^x$) antigens that contain the Type II core, Galβ-1→4GlcNAc unit. Uptake of the free disaccharide was very limited as expected (six hydroxyls), whereas uptake of the peracetylated derivative was nearly as efficient as Xylβ-0-napthol, Table I). Priming was measured by incubating cells with the disaccharides and $^3$H-GlcN, a precursor of amino sugars. A large amount of labeled material was generated on the peracetylated derivative (Table I) in comparison to the non-acetylated disaccharide. Separating the material by anion-exchange chromatography showed that approximately 25% of the $^3$H-oligosaccharides were charged. About 50% of this material was sensitive to NDV sialidase, indicating the presence of α2–3 linked sialic acid residues on a portion of the oligosaccharide chains.

TABLE

| Uptake and priming of Galβ1→4GlcNAcβ-0-naphthalenemethanol and its acetylated derivative in F9 cells | | |
|---|---|---|
| Compound | Uptake (Arbitray units) | Priming ($^3$H-cpm/μg) |
| Xylβ-0-naphthol | 9.0 | ND |
| Galβ1→4GlcNAcβ-0- | 0.5 | 20 |

TABLE-continued

Uptake and priming of Galβ1→4GlcNAcβ-0-naphthalene-methanol and its acetylated derivative in F9 cells

| Compound | Uptake (Arbitray units) | Priming ($^3$H-cpm/μg) |
|---|---|---|
| naphthalenemethanol Acetylated Galβ1→4GlcNAcβ-0-naphthalenemethanol | 6.4 | 250 |

The uptake of Xylβ-0-naphthol, Galβ1→4GlcNAcβ-0-naphthalenemethanol and the peracetylated derivative by F9 cells was measured by a fluorescence assay. The incorporation of [$^3$H]GlcN into oligosaccharaides generated on the primers was measured by absorption to Sep-Pak C18 cartridges. Control incubations without added glycoside yielded fluorescence values of 1.0 and 30 $^3$H-cpm/μg cell protein. These values were subtracted from the data obtained for cells treated with compounds.

Table II provides the common names and structures of the carbohydrates that bind to selectins and mediate cell attachment.

TABLE II

| COMMON NAME | STRUCTURE |
|---|---|
| Sialyl Lewis X (sLe$^x$) | NeuAcα2→3Galβ1→4(Fucα1→3) GlcNAcβ-OR |
| VIM-2 (CD-65) | NeuAcα2→3Galβ1→4GlcNAcβ1-3Galβ1→4(Fucα1→3) GlcNAcβ-OR |
| Sialyl dimeric Lewis X | NeuAcα2→3Galβ1→4(Fucα1-3) GlcNAcβ1-Galβ1→4(Fucα1→3) GlcNAcβ-OR |
| Sialyl Lewis A | NeuAcα2→3Galβ1→3(Fucα1→4) GlcNAcβ-OR |
| 3'-Sulfo Lewis X | SO$_4$-3Galβ1→4(Fucα1→3) GlcNAcβ-OR |
| 3'-Sulfo Lewis A | SO$_4$-3Galβ1→3(Fucα1→4) GlcNAcβ-OR |
| 6'-Sulfo Lewis X | NeuAcα2→3(SO4-6)Galβ1→4(Fucα1→3)GlcNAcβ-OR | where NeuAc is N-acetylneuraminic acid (sialic acid), Gal is galactose, GlcNAc is N-acetylglucosamine, GalNAc is N-acetylgalactosamine, Fuc is fucose and Man is mannose, R = ceramide or glycoprotein.

Figure 4:
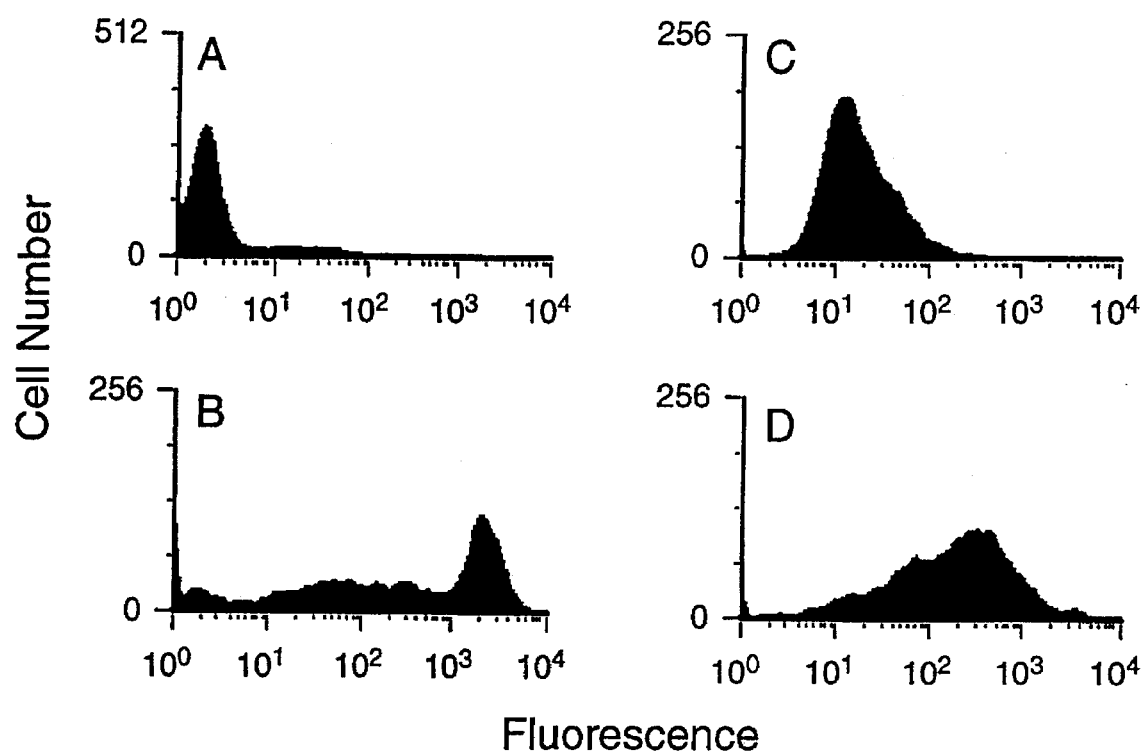
FIG. 4 shows the FACS of HL-60 cells reacted with mAb CSLEX-1. HL-60 cells were grown in the presence or in the absence of 200 μM acetylated Galβ1→4GlcNAcβ-O-naphthalenemethanol (AcLacMAc-NM) for two days. The cells were then treated with CSLEX-1 and subjected to FACS analyses as described below.

Priming on acetylated Galβ1→4GlcNAcβ-0-2-naphthalenemethanol indicated that it would inhibit sLe$^x$ expression on membrane glycoconjugates. To demonstrate this, HL-60 cells were incubated in the presence of 200 μM of the acetylated sugars and the expression of sLe$^x$ on the cell surface was measured by fluorecence activated cell sorting using mAb CSLEX-1 and FITC-labeled goat anti-mouse IgM. The untreated HL-60 population contained approximately 60% of the cells exhibiting strong expression of sLe$^x$ (fluorescence greater than $10^3$) compared to cells treated with a non-specific IgM (compare FIGS. 4A and 4B). Treating the cells with NDV sialidase shifted the entire population to lower fluorescence (FIG. 4C). When the cells were grown in the presence of 200 μM of the acetylated Galβ1→4GlcNAcβ-0-2-naphthalenemethanol, the cell population shifted to a lower mean fluorescence (FIG. 4D). Thus, the novel disaccharide of the present invention inhibited the sLe$^x$ formation on the cell surface.

EXAMPLE 8

AcLacNAc-NM inhibits HL-60 adhesion to human umbilical vein endothelial cells

Figure 5:
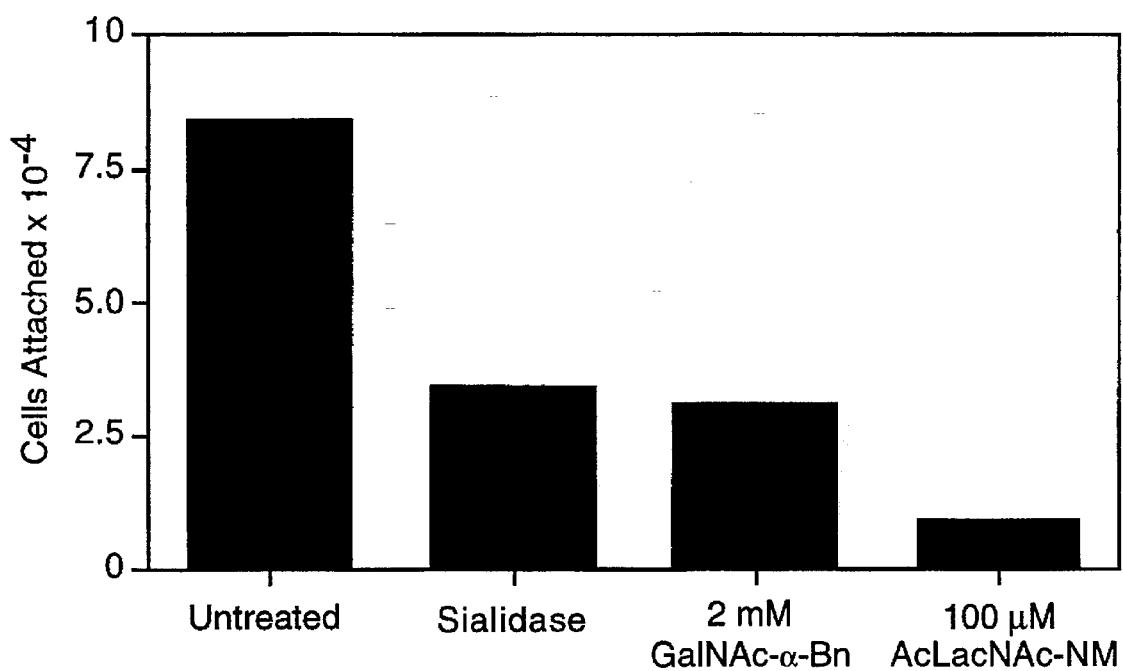
FIG. 5 shows the inhibition of HL-60 adhesion to activated human umbilical vein endothelial cells (HUVEC) by AcLacNAc-NM. HL-60 cells were grown for 44 hours in RPMI-1640 growth medium with 2 μCi/ml of [$^3$H-methyl] thymidine in the presence or absence of 2 mM GalNAcaα-O-Bn or 100 μM AcLacNAc-NM. The cells were harvested by centrifugation and washed to remove glycosides. One set of control cells was treated with NDV-sialidase. The cells were then challenged to adhere to established monolayers of HUVEC (Clonetics, CA) that had been treated for 6 hours with 2 ng/ml of TNF-α. Attachment assays were done at 4'C for 30 minutes under static conditions. The medium was removed and the monolayer was washed three times with growth medium. The monolayer was solubilized in 0.1M NaOH and an aliquot was taken for scintillation counting. The $^3$H-cpm associated with the monolayer was used to calculate the number of attached cells.
Figure 6:
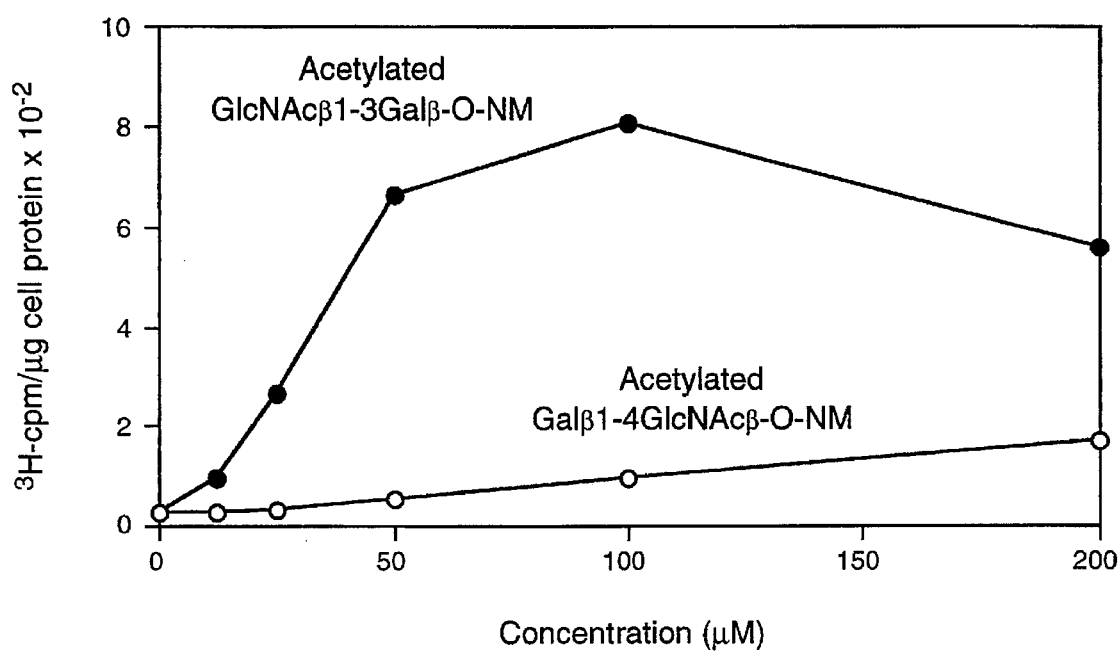
FIG. 6 shows the priming of oligosaccharides on acetylated Galα1-4GlcNAcβ-X-naphthalenemethanol and acetylated GlcNAcβ1-3Galβ-O-naphthalenemethanol in F9 cells. F9 cells were cultured for 58 hours in DMEM medium containing 15 μCi/ml of [6-$^3$H]GlcN and the indicated concentration of acetylated Galβ1-4GlcNAcβ-X-NM or acetylated GlcNAcβ1-3Galβ-X-NM. The growth medium was collected and absorbed to C18 Sep-Pak cartridges.

The diminution of sLe$^x$ on the surface of HL-60 cells indicated that they would not adhere to activated endothelial cells. HUVEC were grown to confluence and stimulated with TNF-α to express E-selectins. HL-60 cells were grown for 2 days with [$^3$H]-thymidine in the presence or absence of AcLacNAc-NM. About 42% of the untreated population of HL-60 cells adhered to HUVEC monolayers and ~3-fold less cells bound if the cells were first treated with NDV sialidase (FIG. 5). Similar results were obtained when the cells were grown in medium containing 2 mM GalNAcα-0-Bn. In contrast, incubating the cells with 100 μM AcLacNAc-NM caused an 8-fold reduction in attached cells. Thus, the reduction of sLe$^x$ on the cell surface measured by FACS (FIG. 4) caused a decrease in static adhesion of HL-60 to HUVEC monolayers (FIG. 5).

EXAMPLE 9

Synthesize glycosides that resemble constituents of sialyl Lewis X

The present invention describes the selection and synthesis of disaccharides that prime oligosaccharides and inhibit the formation of sLe$^x$. These disaccharides resemble intermediates in the initiation, elongation and capping reactions of polylactosaminoglycan and sLe$^x$ assembly. Varying the aglycone and blocking groups on the hydroxyls facilitates entry of the disaccharides into cells. Modifying key hydroxyl groups yields inhibitors of the glycosyltransferases.

sLe$^x$ assembles on core oligosaccharides of glycolipids and O-linked and Asn-linked glycoproteins on the ends of polylactosaminoglycan chains. The first stage of assembly involves forming a branch on O-linked oligosaccharides through the addition of GlcNAcβ1-6 to GalNAc or Gal residues (GlcNAc to GalNAc transferase and GlcNAc transferase(I)). A related reaction in Asn-linked glycoproteins occurs by adding GlcNAcβ1-2 or β1-6 to a mannose residue (GlcNAc transferases II and V, respectively). Polymerization of polylactosaminoglycan chains then takes place by the alternating addition of Galβ1-4 (Galβ1-4 transferase) and GlcNAcβ1-3 (GlcNAc transferase(i)). Capping the terminal Galβ1-4GlcNAc unit (Type II core) by Fucα1-3 to GlcNAc (Fucα1-3 and Fucα1-3/4 transferases) and NeuAcα2-3 to Gal (sialylα2-3 transferase) yields sLe$^x$.

Many of the enzymes that initiate, polymerize and cap polylactosaminoglycan chains use disaccharides as substrates. In some cases the disaccharides have higher Km values than larger oligosaccharides, but nevertheless the disaccharides have activity. Furthermore, the ability of an enzyme to use a particular substrate may differ when the enzyme is membrane-bound in an intact cell compared to being solubilized in detergent micelles in vitro.

Disaccharides that resemble intermediates on which branching occurs may not prove effective as primers since the GlcNAc transferase (I) and GlcNAc transferase II use trisaccharides or larger oligosaccharides as acceptors. The GlcNAc to GalNAc transferase will use Galβ1-3GalNAcα-OR in vitro and GlcNAc transferase V will use GlcNAcβ1-2Manβ-OR. Disaccharides that contain the first GlcNAc residue bypass the need for GlcNAc transferase (I) and GlcNAc transferase II. Galβ1-4 transferase will add to substrates bearing a terminal GlcNAc residue without much specificity for the group attached to the anomeric carbon.

Galβ1-4 transferase and GlcNAc transferase (i) (GlcNAcβ1-3 to Gal) catalyze elongation of polylactosaminoglycans. GlcNAc transferase (i) will use Galβ1-4GlcNAc as a substrate in vitro, which probably explains why AcLacNAc-NM primed oligosaccharides in F9 cells.

Summary of disaccharide primers

| Branching | Elongation | Capping |
|---|---|---|
| Galβ1-3GalNAcα-OR | GlcNAcβ1-6GalNAcα-OR | Galβ1-4GlcNAcβ-OR |
| | GlcNAcβ1-6Galβ-OR | |
| | GlcNAcβ1-2Manα-OR | |
| | GlcNAcβ1-6Manα-OR | |
| | GlcNAcβ1-2Manα-OR | |
| | Galβ1-4GlcNAcβ-OR | |
| | GlcNAcβ1-3Galβ-OR | |

Disaccharide synthesis takes advantage of blocking, coupling and deblocking techniques common in synthetic carbohydrate chemistry. The reducing terminal sugar is coupled to an aglycone and suitably protected so that a second sugar can be added in a regio and stereoselective manner. If problems with selective addition are encountered, enzymatic glycosylation can be used. Cloning studies have made available many of the enzymes involved in polylactosaminoglycan and sLe$^x$ biosyntheses. $^{13}$C NMR, 1-D and 2-D 1H NMR, elemental analysis, and mass spectrometry are used to confirm the structure of the compounds.

Naphthalenemethanol was used as an aglycone in the novel disaccharide inflammation antagonists of the present invention for several reasons. First, cells take up AcLacNAc-NM nearly as well as non-acetylated pentosides linked to naphthol (e.g., β-D-xylosides). Second, the hydrophobicity of the aglycone allows attached saccharides up to six or more sugars to bind to C18 Sep Pak cartridges in the presence of high salt. Third, the naphthalene ring fluoresces, which allows detection of very small amounts of product. Fourth, aliphatic chains can act like detergents. The coupling efficiency also is high (70–80%). However, a person having ordinary skill in this art would readily recognize that the aglycone could alternatively be selected from the group consisting of naphthol, naphthalenemethane, indenol, a heterocyclic derivative of indenol, a heterocyclic derivative of naphthol and a heterocyclic derivative of naphthalenemethanol.

One possible problem concerns the stability of the disaccharides in vivo. Cells contain glycosidases that can remove terminal galactose (β-galactosidase) and GlcNAc (β-hexosaminidase). Replacing the glycosidic oxygen with nitrogen, sulfur or carbon renders them less susceptible to glycosidases. C-, N-, and S-xylosides prime glycosaminoglycans like their O-linked counterpart.

An acetyl group was used to block the hydrophilic hydroxyls of Galβ1-4GlcNAcp-X-NM. A significant lag phase preceded priming of oligosaccharides on AcLacNAc-NM in F9 cells, which may reflect slow deacetylation and accumulation of free disaccharide. Other acyl groups might prove more effective, such as butyryl or hexanoyl groups. Longer acyl chains also might permit using fewer blocking groups, and cells might activate partially acylated disaccharides more rapidly.

Other ways exist to enhance the rate of removal of blocking groups. Trichloroacetate esters (CCl$_3$COO-sugar) hydrolyze more rapidly than acetate esters because of the electron withdrawing property of chlorine. Acetyl succinate esters (AcOCO[CH$_2$]$_2$COO-sugar) also improves hydrolysis since the succinate moiety places the acetyl group farther away from the sugar, avoiding steric problems that might occur with the acetates linked directly to the sugar. Hydrolysis of the acetate facilitates rapid intramolecular hydrolysis of the succinate ester with formation of succinic anhydride and the free sugar. Acetoxymethyl esters (AcOCH$_2$O-sugar) and other carbonoyloxy analogs are effective as well, since cellular esterases hydrolyze them readily.

EXAMPLE 10

Glycosides for inhibition of sLe$^x$ assembly and priming activity

The present invention describes the use of disaccharides as primers and inhibitors of sLe$^x$ in cultured cells. The oligosaccharides generated on the primers are analyzed and truncated oligosaccharides accumulatating on endogenous glycoconjugates is measured. Antibody based assays detect the inhibition of sLe$^x$ expression on cell surfaces and quantitative ELISAs is used to determine an ED$^{50}$ for each compound.

The concentration of each compound is varied between 0.1–100 µM and the amount of labeled oligosaccharide is measured. Peracetylated GlcNAcβ1-3Galβ-0-naphthalenemethanol (AcGlcNAcGal-NM) was made and the priming results are shown in FIG. 3. This disaccharide was much more active than AcLacNAc-NM at low dose and at >25 µM it primed nearly 10-fold more [$^3$H]GlcN-labeled oligosaccharides.

About 25% of the isolated [6-$^3$H]GlcN labeled oligosaccharides primed on AcLacNAc-NM bound to QAE-Sephadex and eluted in the position of −1 charged species. Treatment with NDV sialidase showed that about half of the material contained α2-3 linked sialic acid. The remainder may consist of α2-6 linked sialic acid or sulfated oligosaccharides. Additional labeling studies using [6-$^3$H]Fuc and [2-$^3$H]Man followed by treatment with specific glycosidases shows the presence and linkage of fucose and sialic acid residues (almond meal fucosidase, α1-3 and α1-4 linked fucose to GlcNAc; chicken liver fucosidase, α1-2, α1-4 and α1-6 linked fucose to GlcNAc; NDV sialidase, α2-3 linked sialic acids; and Arthrobacter sialidase, α2-3 and α2-6 linked sialic acids). Extension products (Gal and GlcNAc addition) are assessed by gel filtration coupled with treatment with β-galactosidase, endo-β-galactosidase or β-hexosaminidase and lectin chromatography (tomato and potato lectins).

Active glycosides compete with endogenous intermediates and cause the accumulation of glycoproteins and glycolipids with truncated oligosaccharide chains. The non-reducing termini that become exposed depend on the primer and its potency. Glycoside-treated and control cells are incubated with different amounts of various lectins to measure the concentration where cell growth declines to about 10% of that observed without lectin. The following lectins in past studies have shown that glycosaminoglycan-deficient mutants make normal glycoproteins and glycolipids: *Phaseolus vulgaris* leukoagglutinin (Galβ1-4GlcNAcβ1-2Manα1-6[GlcNAcβ1-2Manα1-3]Man), wheat germ agglutinins from *Triticum vulgaris* (terminal sialic acids or GlcNAc residues), Concanavalin A from *Canavalia ensiformis* (branched Man residues), ricin toxin from *Ricinus communis* (terminal Gal or GalNAc residues), *Lens culinaris* agglutinin (branched Man residues with αlinked fucose), *Lycopersicon esculentum* agglutinin (tomato) (GlcNAcβ1-4Gal polymers), and *Solanum tuberosum* agglutinin (potato) (GlcNAcβ1-4Gal polymers).

Cells are grown in the presence of various amounts of disaccharides and analyzed for reactivity to CSLEX-1 using fluorescence activated cell sorting. The optimal concentration of primary and secondary antibodies and the specificity of the assays has been established already for HL-60 cells. HL-60 human promyelocytic leukemia cells and U-937 human monocytic cells produce sLe$^x$ constitutively when grown in suspension culture. Primary human monocytes and neutrophils carry sLe$^x$ primarily linked to O-linked polylactosaminoglycans.

F9 cells produce polylactosaminoglycans when grown on gelatin-coated surfaces. Treatment with retinoic acid induces differentiation of the cells, causes spheroids to form, increases the expression of sLe$^x$. Treating the spheroids with EDTA dissociates them to single cells that can be sorted. Alternatively, the intact spheroids can be examined by fluorescence microscopy.

Measuring the amount of sLe$^x$ in cell extracts provides a way to determine an ED$_{50}$ value for each disaccharide. An ELISA is used to quantify sLe$^x$ in cell extracts and purified glycolipid and glycoprotein fractions. Samples are spotted on PVDF membranes (Millipore), reacted with CSLEX-1, and then with a goat antimouse IgM antibody conjugated to peroxidase. The intensity of product formation is compared to a standard curve constructed with different amounts of an sLe$^x$-BSA conjugate (oxford Glycosystems). Treating glycoproteins with O-glycosidase or PNGase F distinguishes sLe$^x$ on O-linked and N-linked chains. Plotting the amount of residual sLe$^x$versus glycoside concentration yields an ED$_{50}$ value for each disaccharide primer, which will be compared to the ED$_{50}$ values for inhibiting cell adhesion.

EXAMPLE 11

Glycosides inhibit adhesion of leukocytes to selectins and stimulated endothelial cells The present invention also demonstrates the effect of disaccharide primers on cell adhesion. The attachment of HL-60, U-937, and primary neutrophils and monocytes to monolayers of stimulated HUVEC was demonstrated. A centrifugation assay allows measurement of ED$_{50}$ values for inhibiting adhesion. Dynamic adhesion assays in which the cells adhere under shear stress shows the efficacy of the disaccharides under more physiological conditions. Acetylated GlcNAcβ1→3Galβ-O-naphthalenemethanol inhibited cell adhesion at concentrations of less than 25 µM. Thus, this compound primes oligosaccharides and inhibits cell adhesion more efficiently than acetylated Galβ1→4GlcNAcβ-X-naphthalenemethanol.

EXAMPLE 12

Adhesion of leukocytes to HUVEC

Inflammatory cytokines, such as TNF-α and IL-1, activate HUVEC and increase the expression of E-selectin. In contrast, treating HUVEC with thrombin or histamine stimulates expression of P-selectin. Thus, the adhesion of leukocytes to different selectins on cells is measured by choosing different cytokines. Adhesion to activated HUVEC better approximates conditions encountered by leukocytes in blood vessels. HL-60 cells adhere to confluent HUVEC monolayers that had been treated with TNF-α. About 40% of the added cells bound and treatment with NDV sialidase or AcLacNAc-NM reduced adhesion.

EXAMPLE 13

Anti-inflammatory activity of the novel disaccharide antagonists in animal models of rheumatoid arthritis Mice immunized with bovine Type II collagen develop a progressive inflammatory arthritis with pathological and immunological features resembling rheumatoid arthritis. Symptoms manifest as edema and erythema in the paw, causing an increase in its width. Synovial thickening, pannus formation and cartilage erosion also occurs. Apparently, antibodies raised to the injected connective tissue components cross react with homologous mouse proteins. Adoptive transfer experiments indicate a cellular immune component in the inflammatory reaction as well. Measuring the number of affected paws and paw width followed by histological analysis of affected limbs illustrates the efficacy of the disaccharides. The leukocytes from treated animals are examined to show differences in expression of sLe$^x$ and their ability to adhere to HUVEC.

To show tolerance to the disaccharides, the compounds are emulsified in mineral oil or carboxylmethylcellulose and injected i.p. (1–100 mg/kg) at intervals of three days for up to four weeks. Any changes in behavior, distress and weight is noted. Blood samples are taken periodically to measure standard blood chemistry.

Mice are immunized intra-dermally at the base of tail with 100 µg of bovine Type II collagen in Freund's complete adjuvant. Mice usually develop symptoms of arthritis 3–8 weeks after immunization. They are pre-bled, bled at the onset of disease and at two week intervals to titer serum antibody to the immunogen using an ELISA. Control animals are injected with adjuvant alone. Those animals exhibiting an antibody response to the immunogen and symptoms of arthritis are used for the following dosing schedule. Five groups of animals (three animals each) receive a disaccharide of the present invention emulsified in carboxymethylcellulose or mineral oil and five groups will receive vehicle. A control group is sacrificed before beginning treatment to establish a base line. Additional groups are sacrificed at weeks 2, 4, 6, and 8. Another group of animals is treated for 4 weeks and then followed for 4 more weeks to measure rebound from treatment. The number of involved paws exhibiting edema is counted and paw width is measured three times per week. Efficacy is judged by a reduction in the number of involved paws and by a reduction in average paw width measurements.

Over twenty years ago, Okayama et al. showed that cells will take up β-D-xylosides and prime glycosaminoglycan and proteoglycan biosynthesis. In a similar way, α-N-acetyl-galactosaminides will prime mucin-like oligosaccharides and alter the assembly of O-linked oligosaccharides on glycoproteins. The present invention shows that the uptake of these compounds occurs by diffusion. The ability to produce oligosaccharide chains on these primers implies that the compounds diffuse across the plasma membrane and into the endoplasmic reticulum/Golgi network as well. They may diffuse into all cell compartments equally, but some preferential sorting may also occur.

More complex saccharides were not taken up and the present invention shows that the number of hydroxyl groups in the glycan determines the rate and extent of uptake. Thus, pentosides (L-Araα-0-2-naphthol and Xylβ-0-2-naphthol) diffuse more readily than hexosides (Galβ-0-naphthol) containing the same aglycone, showing that only one additional hydroxyl group poses a major obstacle to uptake. Presumably, this difference reflects the difficulty of passing the polar hydroxyl group through the interior of a membrane which resembles a low dielectric solvent. The multiple hydroxyl groups present in a disaccharide and larger oligosaccharides provide an even larger diffusion barrier to surpass.

A strong correlation exists between membrane permeability and partitioning of solutes into an organic solvent. Thus, increasing the hydrophobicity of the aglycone should increase uptake. Although this was true for galactose, attaching phenanthrol to a disaccharide did not improve its uptake. Increasing the size and hydrophobicity of the aglycone further should enhance uptake, but strongly amphipathic compounds act like detergents. Thus, pyrene derivatives (having 4 fused aromatic rings) and glycosides containing alkyl chains of greater than 8 carbon atoms cause cell lysis.

To circumvent this problem, a modification of the sugar residues was created to facilitate uptake. Acylation has been used to improve availability of drugs, e.g., acetylsalicylic acid), second messengers (e.g., dibutyryl cAMP) and glycosidase inhibitors (e.g., carbonyloxy analog of swainsonine). Cells have numerous esterases that can remove the acyl groups and convert these compounds into their active forms. The present invention shows that one or more of these enzymes reside in the lumen of the endoplasmic reticulum/Golgi network since the disaccharides presumably had to retain the acetyl groups for entry into this compartment. Priming of oligosaccharide chains on Galβ1→4GlcNAcβ-0-naphthalenemethanol increases with time and does not saturate for several hours. Thus, both the rates of diffusion and deacetylation will affect the efficiency of priming. The affinity of the disaccharide substrate for its target glycosyltransferase also plays a role.

The usefulness of acetylated disaccharides was shown, in part, by the inhibition of sLe$^x$ expression on the surface of HL-60 cells by acetylated Galβ1→4GlcNAcβ-0-2-naphthalenemethanol. Inhibition probably occurred by blocking the formation of sLe$^x$ on O-linked oligosaccharides of glycoproteins. The decrease in sLe$^x$ expression had a corresponding effect on cell adhesion mediated through sLe$^x$-selectin interactions.

Other disaccharides that resemble parts of Asn-linked and O-linked oligosaccharides of glycoproteins, glycoaminoglycan chains of proteoglycans and the oligosaccharides of glycolipids would be useful as primers. Analogs of acetylated disaccharides attached to an appropriate aglycone would also provide a source of inhibitors.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An acetylated disaccharide having the structure sugar - sugar - X - R wherein said sugars are selected from the group consisting of N-acetylneuraminic acid, galactose, N-acetylglucosamine, N-acetylgalactosamine, fucose, and mannose, with the proviso that at least one sugar is N-acetylneuraminic acid, N-acetylglucosamine, or N-acetylgalactosamine;

wherein X is a bridging atom selected from the group consisting of oxygen, sulfur, nitrogen, and carbon; and wherein R is an aglycone selected from the group consisting of naphthol, naphthalenemethane, and indenol.

2. An acetylated disaccharide having the structure sugar - sugar - X - R wherein said sugars are selected from the group consisting of N-acetylneuraminic acid, galactose, N-acetylglucosamine, N-acetylgalactosamine, fucose, and mannose, with the proviso that at least one sugar is N-acetylneuraminic acid, N-acetylglucosamine, or N-acetylgalactosamine, and with the proviso that a hydroxyl group of one of the sugars is replaced with a methoxy group;

wherein X is a bridging atom selected from the group consisting of oxygen, sulfur, nitrogen, and carbon; and wherein R is an aglycone selected from the group consisting of naphthol, naphthalenemethane, and indenol.

3. An acetylated disaccharide having the structure sugar - sugar - X - R wherein said sugars are selected from the group consisting of N-acetylneuraminic acid, galactose, N-acetylglucosamine, N-acetylgalactosamine, fucose, and mannose, with the proviso that at least one sugar is N-acetylneuraminic acid, N-acetylglucosamine, or N-acetylgalactosamine, and with the proviso that sulfur is substituted for either an exocyclic oxygen or a ring oxygen of a sugar;

wherein X is a bridging atom selected from the group consisting of oxygen, sulfur, nitrogen, and carbon; and wherein R is an aglycone selected from the group consisting of naphthol, naphthalenemethane, and indenol.

4. The acetylated disaccharide of claim 1 having the structure

N-acetylglucosamine-β1→6N-acetylglucosamine-α-X-R wherein X is a bridging atom selected from the group consisting of oxygen, sulfur, nitrogen, and carbon; and wherein R is an aglycone selected from the group consisting of naphthol, naphthalenemethane, and indenol.

5. The acetylated disaccharide of claim 1 having the structure

N-acetylglucosamine-β1→6N-galactose-β-X-R wherein X is a bridging atom selected from the group consisting of oxygen, sulfur, nitrogen, and carbon; and wherein R is an aglycone selected from the group consisting of naphthol, naphthalenemethane, and indenol.

6. The acetylated disaccharide of claim 1 having the structure

N-acetylglucosamine-β1→6N-mannose-α-X-R wherein X is a bridging atom selected from the group consisting of oxygen, sulfur, nitrogen, and carbon; and wherein R is an aglycone selected from the group consisting of naphthol, naphthalenemethane, and indenol.

7. The acetylated disaccharide of claim 1 having the structure

N-acetylglucosamine-β1→2N-mannose-α-X-R wherein X is a bridging atom selected from the group consisting of oxygen, sulfur, nitrogen, and carbon; and wherein R is an aglycone selected from the group consisting of naphthol, naphthalenemethane, and indenol.

8. The acetylated disaccharide of claim 1 having the structure galactose-β1→3-N-acetylgalactosamine-α-X-R wherein X is a bridging atom selected from the group consisting of oxygen, sulfur, nitrogen, and carbon; and wherein R is an aglycone selected from the group consisting of naphthol, naphthalenemethane, and indenol.

9. The acetylated disaccharide of claim 1 having the structure galactose-β1→4-N-acetylglucosamine-β-X-R wherein X is a bridging atom selected from the group consisting of oxygen, sulfur, nitrogen, and carbon; and wherein R is an aglycone selected from the group consisting of naphthol, naphthalenemethane, and indenol.

10. The acetylated disaccharide of claim 1 having the structure fucose-α1→3-N-acetylglucosamine-β-X-R wherein X is a bridging atom selected from the group consisting of oxygen, sulfur, nitrogen, and carbon; and wherein R is an aglycone selected from the group consisting of naphthol, naphthalenemethane, and indenol.

11. The acetylated disaccharide of claim 1 having the structure fucose-α1→4-N-acetylglucosamine-β-X-R wherein X is a bridging atom selected from the group consisting of oxygen, sulfur, nitrogen, and carbon; and wherein R is an aglycone selected from the group consisting of naphthol, naphthalenemethane, and indenol.

12. A pharmaceutical composition comprising an acetylated disaccharide of claim 1, 2, or 3, and a pharmaceutically acceptable carrier.

13. A method of treating an inflammatory disease in an individual comprising the step of administering to said individual a therapeutically effective dose of the composition of claim 12.

14. The method of claim 13 wherein said inflammatory disease is selected from the group consisting of acute inflammatory diseases and chronic inflammatory diseases.

15. The method of claim 14 wherein said acute inflammatory disease is selected from the group consisting of appendicitis, tonsillitis, delayed hypersensitivity reactions, inflammation due to sepsis, cutaneous inflammation, and ischemic reperfusion injury.

16. The method of claim 14 wherein said chronic inflammatory disease is rheumatoid arthritis.

17. The method of claim 13, wherein said composition is administered in a dose of from about 0.1 mg/kg to about 20 mg/kg.

18. A method of inhibiting the synthesis of a naturally occurring selectin-binding saccharide in a cell, comprising the step of contacting said cell with a pharmacologically effective amount of the acetylated disaccharide of claim 1, 2, or 3.

* * * * *